United States Patent [19]

Regnier et al.

[11] Patent Number: 5,627,205
[45] Date of Patent: May 6, 1997

[54] SUBSTITUTED PHENOXYISOBUTYRIC ACIDS AND ESTERS

[75] Inventors: Gilbert Regnier, Chatenay Malabry; Claude Guillonneau, Clamart; Jean-Paul Vilaine, Chatenay Malabry; Albert Lenaers, Triel sur Seine; Christine Breugnot, Paris, all of France

[73] Assignee: Adir Et Compagnie, Courbevoie, France

[21] Appl. No.: 510,857

[22] Filed: Aug. 3, 1995

Related U.S. Application Data

[62] Division of Ser. No. 230,143, Apr. 19, 1994, Pat. No. 5,512,595.

[30] Foreign Application Priority Data

Apr. 20, 1993 [FR] France ................................. 93 04606

[51] Int. Cl.$^6$ .......................... A61K 31/35; A61K 31/34; C07D 311/72; C07D 307/80
[52] U.S. Cl. ...................... 514/456; 514/469; 549/406; 549/408; 549/410; 549/462; 549/469; 549/470
[58] Field of Search ................................. 549/406, 408, 549/410, 469, 470, 462; 514/456, 469

[56] References Cited

PUBLICATIONS

Role of Oxidized Low Density Lipoprotein in Atherogenesis by Witztum, et al., J. Clin. Invest. vol. 88, pp. 1785–1792 (Dec. 1991).
Malondialdehyde–modified Low Density Lipoproteins in Patients with Atherosclerotic Disease by Holvoet, et al., J. Clin. Invest., vol. 95, pp. 2611–2619 (Jun. 1995).
Increased Susceptibility of Lipid Oxidation to Low–Density Lipoproteins and Erythrocyte Membranes From Diabetic Patients by Rabini, et al., Metabolism, vol. 43, No. 12, pp. 1470–1474 (Dec. 1994).

Serum Antioxidants and Myocardial Infarction by Street, et al., American Heart Association, Inc., pp. 1154–1161 (1994).

Antioxidant vitamins and coronary heart disease risk by Clifton, Division of Human Nutrition, Commonwealth Scientific and Industrial Research Organisation, Adelaide, Australia, Current Opinion in Lipidology 1995, 6:20–24.

Effect of Alpha–tocopherol on Restenosis after Angioplasty in a Model of Experimental Atherosclerosis by Lafont, et al., J. Clin. Invest., vol. 95, pp. 1018–1025 (Mar. 1995).

Immunization of low density lipoprotein (LDL) receptor–deficient rabbits with homologous malondialdehyde–modified LDL reduces atherogenesis by Palinski, et al., Proc. Natl. Acad. Sci. USA, vol. 92, pp. 821–825 (Jan. 1995) Medical Sciences.

*Primary Examiner*—Nicky Chan
*Attorney, Agent, or Firm*—The Firm of Gordon W. Hueschen

[57] ABSTRACT

New substituted phenoxyisobutyric acids and esters that can be used as medicaments and correspond to the formula:

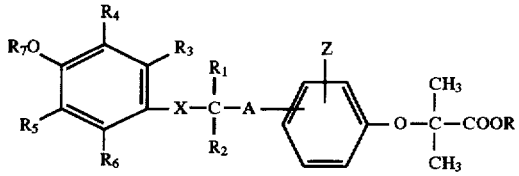

wherein X, A, R, $R_1$, $R_2$, $R_3$, $R_4$, $R_5$, $R_6$, $R_7$ and Z are as defined in the description.

Those compounds and their physiologically tolerable salts can be used therapeutically.

5 Claims, 3 Drawing Sheets

SUBSTITUTED PHENOXYISOBUTYRIC ACIDS AND ESTERS

The present application is a division of our prior-filed application Ser. No. 08/230,143, filed Apr. 19, 1994, now U.S. Pat. No. 5,512,595.

The present invention relates to new substituted phenoxyisobutyric acids and esters, to a process for the preparation thereof and to pharmaceutical compositions containing them.

It relates more especially to substituted phenoxyisobutyric acids and esters of formula I:

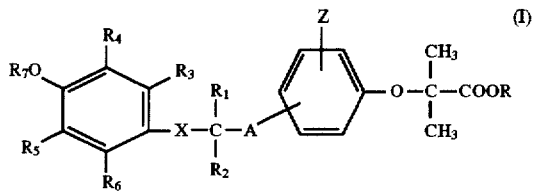

wherein:

X represents an oxygen atom, a sulphur atom or a single bond;

A represents a single bond or a hydrocarbon radical containing from 1 to 9 carbon atoms in a straight or branched chain optionally including a double bond, a cyclopropyl radical, an oxygen atom or a carbonyl radical, or optionally substituted by a halogen atom (such as, for example, chlorine or bromine) or a hydroxy radical;

R represents a hydrogen atom or an alkyl radical that has from 1 to 6 carbon atoms in a straight or branched chain and is optionally substituted by one or two hydroxy radicals;

$R_1$ and $R_3$:
  each simultaneously represents a hydrogen atom, or together form a $(CH_2)_n$ bridge wherein n is 1 or 2, or $R_1$ represents:
  a methyl radical, or
  a single bond forming a double bond with the group A when that group is a hydrocarbon radical, and in each of those cases, $R_3$ simultaneously represents a hydrogen atom;

each of $R_2$ and $R_6$, which may be identical or different, represents a hydrogen atom or a methyl radical;

each of $R_4$ and $R_5$, which may be identical or different, represents an alkyl radical having from 1 to 6 carbon atoms in a straight or branched chain;

$R_7$ represents a hydrogen atom or a labile protecting grouping, such as, for example, a $CH_3CO$—, $C_2H_5O$—$CH_2$— or benzyl radical; and Z represents a hydrogen or halogen atom or an alkyl or alkoxy radical each containing from 1 to 5 carbon atoms in a straight or branched chain.

Some of the compounds of formula I contain one or more chiral atoms and can therefore exist in the form of enantiomers or diastereoisomers which also form part of the present invention.

Equally, the compounds of formula I wherein R represents a hydrogen atom can be converted into addition salts with pharmaceutically acceptable bases, which salts, as such, are included in the present invention.

The prior art closest to the present invention is illustrated by U.S. Pat. No. 4,752,616 which relates, inter alia, to thioalkylphenylalkanoic acids and esters of the formula:

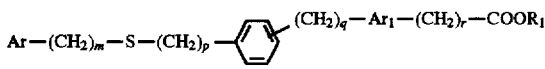

wherein:

Ar represents, inter alia, an optionally substituted phenyl radical;

$A_1$ is a group of the formula:

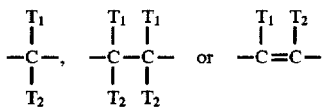

($T_1$ and $T_2$ being hydrogen or lower alkyl);

m is zero, 1, 2 or 3;

p is an integer from 1 to 5;

q is zero, 1, 2 or 3;

r is zero, 1 or 2, and $R_1$ is hydrogen, lower alkyl or an alkali metal.

The said compounds are anti-thrombotic, anti-asthmatic and vasodilatory agents.

The compounds of the present invention differ from the previously known compounds defined above both in their chemical structure and in their pharmacological and therapeutic activity which results from their anti-oxidant effect demonstrated in respect of human LDL (low-density lipoproteins) and their potential hypolipaemic effect.

REFERENCE TO THE DRAWINGS

Reference is now made to the drawings for a better understanding of the invention, wherein FIGS. 1, 2, and 3 illustrate the advantageous antioxidant effects of the compounds of the invention.

FIG. 1 illustrates the peroxidation of LDL by $CuSO_4$ $5.10^{-6}M$ and compares the effect of the compound of Example 1 with the effect of probucol.

In this comparison, as shown in TABLE A, compounds of other Examples show the same advantageous effect when compared with probucol as well as with Vitamin E.

Figure 1:
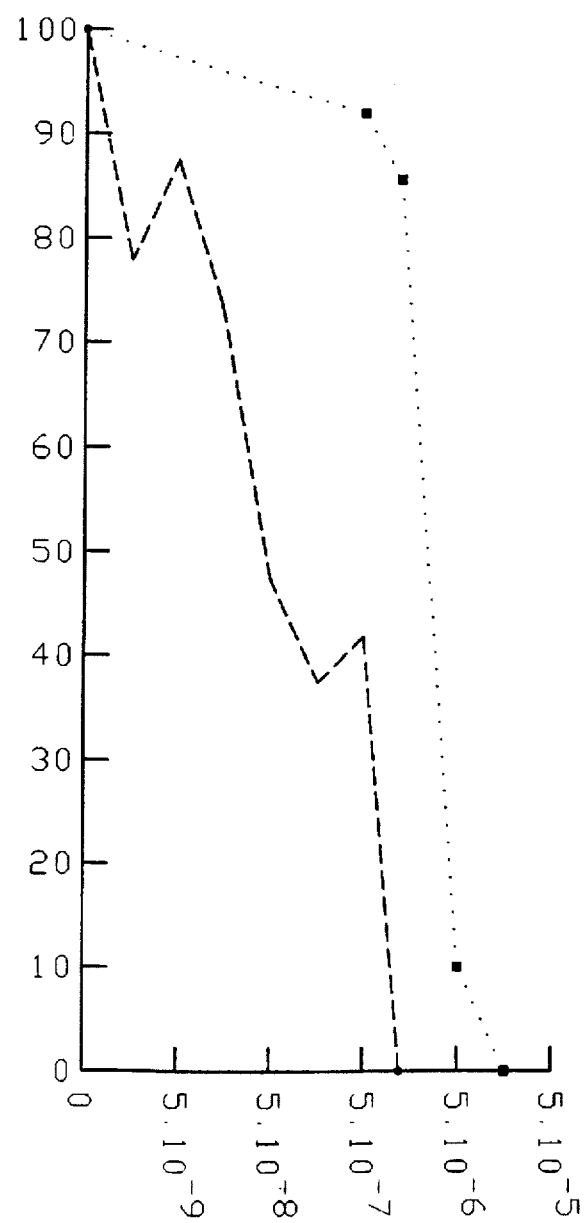

The present invention relates also to a process for the preparation of the compounds of formula I, characterised in that:

a). a compound of formula IIa:

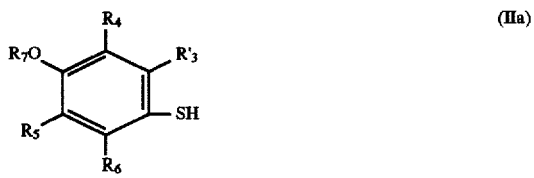

(IIa)

wherein:

$R_4$, $R_5$, $R_6$ and $R_7$ are as defined above, and $R'_3$ represents a hydrogen atom, is reacted with a compound of formula IIIa:

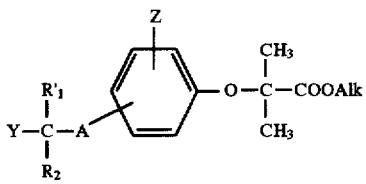
(IIIa)

wherein:

R$_2$, A and Z are as defined above;

R'$_1$ represents a hydrogen atom or a methyl radical;

Alk represents an alkyl radical having from 1 to 6 carbon atoms in a straight or branched chain, and Y represents a chlorine or bromine atom;

to obtain a compound of formula Ia$_1$:

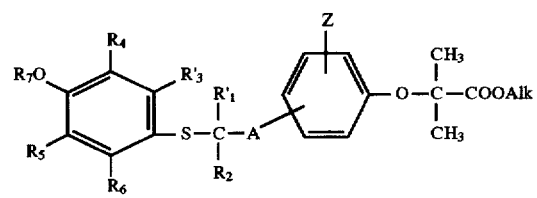
(Ia$_1$)

wherein R'$_1$, R$_2$, R'$_3$, R$_4$, R$_5$, R$_6$, R$_7$, A, Z and Alk are as defined above, which compound of Ia$_1$ is, depending on the nature of R$_7$, converted by sequential methods of saponification, hydrolysis or hydrogenolysis into a compound of formula Ia$_2$:

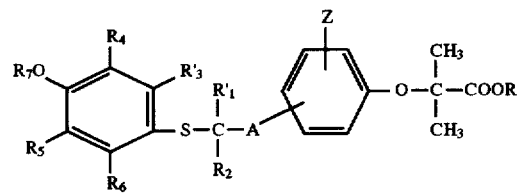
(Ia$_2$)

wherein R'$_1$, R$_2$, R'$_3$, R$_4$, R$_5$, R$_6$, R$_7$, A, Z and R are as defined above, or b). a compound of formula IIb:

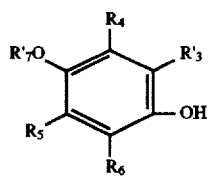
(IIb)

wherein:

R'$_3$, R$_4$, R$_5$ and R$_6$ are as defined above and

R'$_7$ represents a labile protecting grouping, such as: CH$_3$CO—, C$_2$H$_5$—O—CH$_2$— or benzyl; is reacted with a compound of formula IIIb:

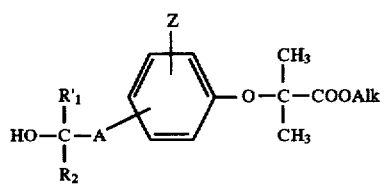
(IIIb)

wherein R'$_1$, R$_2$, A, Z and Alk are as defined above, to obtain a compound of formula Ib$_1$:

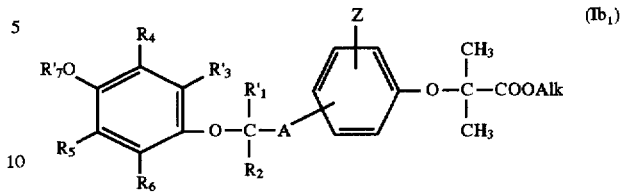
(Ib$_1$)

wherein R'$_1$, R$_2$, R'$_3$, R$_4$, R$_5$, R$_6$, R'$_7$, A, Z and Alk are as defined above.

which compound of formula Ib$_1$ is, depending on the nature of R'$_7$, converted by sequential methods of saponification, hydrolysis or hydrogenolysis into a compound of formula Ib$_2$:

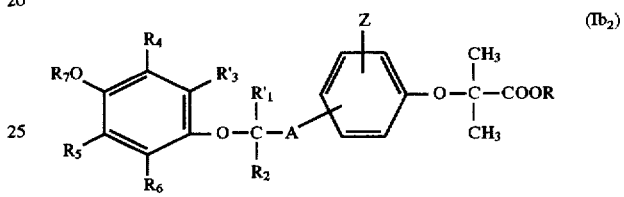
(Ib$_2$)

wherein R'$_1$, R$_2$, R'$_3$, R$_4$, R$_5$, R$_6$, R$_7$, A, Z and R are as defined above; or c). a compound of formula IIc:

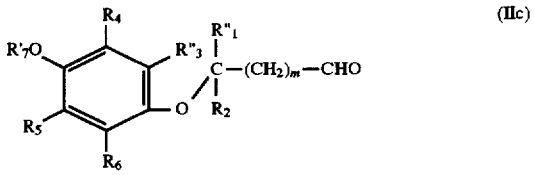
(IIc)

wherein:

R$_2$, R$_4$, R$_5$, R$_6$ and R'$_7$ are as defined above,

R"$_1$ and R"$_3$ together represent a (CH$_2$)$_n$ bridge wherein n is as defined above, and m represents zero or an integer from 1 to 5; is reacted with a compound of formula IIIc:

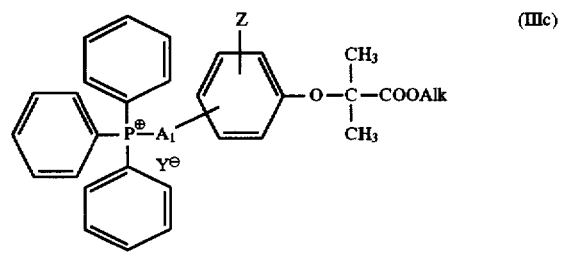
(IIIc)

wherein:

Alk and Z and Y are as defined above,

A$_1$ represents a single bond or a hydrocarbon radical containing from 1 to 3 carbon atoms in a straight or branched chain;

to obtain a compound of formula Ic$_1$:

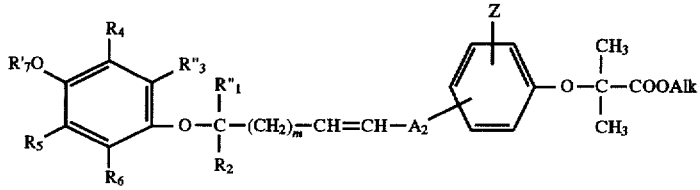

wherein:

R"$_1$, R$_2$, R"$_3$, R$_4$, R$_5$, R$_6$, R'$_7$, m, Z and Alk are as defined above, and A$_2$ represents a single bond or a hydrocarbon radical containing 1 or 2 carbon atoms in a straight or branched chain; p2 which compound of formula Ic$_1$ is reduced to obtain the compound of formula Ic$_2$:

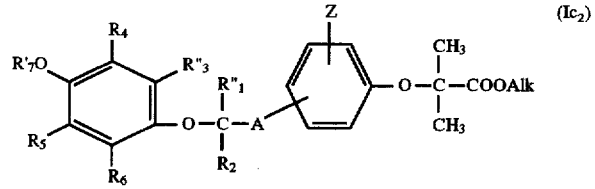

wherein R"$_1$, R$_2$, R"$_3$, R$_4$, R$_5$, R$_6$, R'$_7$, A Z and Alk are as defined above;

which compound of formula Ic$_2$ is, depending on the nature of R'$_7$, converted by sequential methods of saponification, hydrolysis or hydrogenolysis into a compound of formula Ic$_3$:

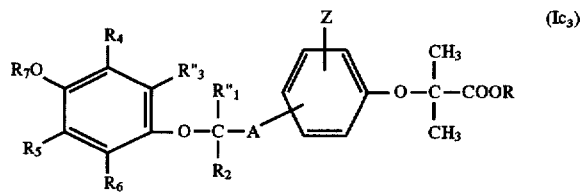

wherein R"$_1$, R$_2$, R"$_3$, R$_4$, R$_5$, R$_6$, R'$_7$, A, Z and R are as defined above; or d). a compound of formula IId):

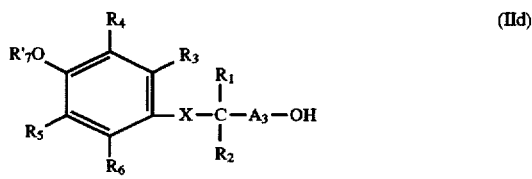

wherein:

R$_1$, R$_2$, R$_3$, R$_4$, R$_5$, R$_6$, R'$_7$ and X are as defined above, and A$_3$ represents a single bond or a hydrocarbon radical containing from 1 to 9 carbon atoms in a straight or branched chain, is reacted with a compound of formula IIId:

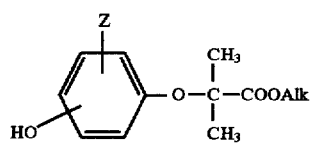

wherein Z and Alk are as defined above, to obtain a compound of formula Id$_1$:

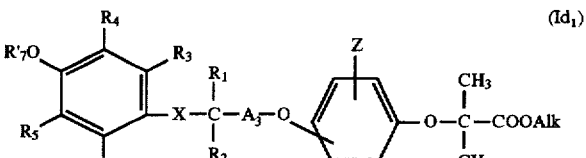

wherein R$_1$, R$_2$, R$_3$, R$_4$, R$_5$, R$_6$, R'$_7$, X, A$_3$ and Alk are as defined above;

which compound of formula Id$_1$ defined above may be saponified, hydrogenolysed or hydrolysed to give the corresponding acid of formula Id$_2$:

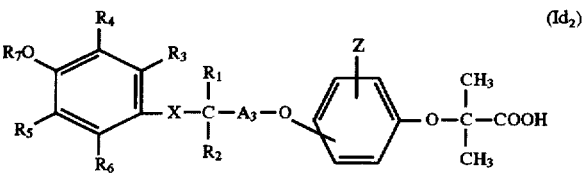

wherein R$_1$, R$_2$, R$_3$, R$_4$, R$_5$, R$_6$, R$_7$, X, R$_3$ and Z are as defined above; or e). a compound of formula IIe:

wherein:

R$_3$, R$_4$, R$_5$, R$_6$ and R$_7$ are as defined above, and

X' represents an oxygen or sulphur atom, is reacted with a compound of formula IIIe:

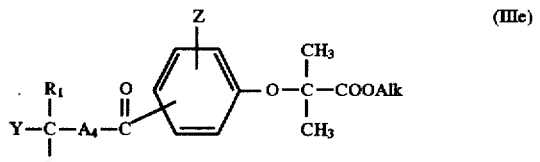

wherein:

Y, R$_1$, R$_2$, Z and Alk are as defined above, and

A$_4$ represents a single bond or a hydrocarbon radical having from 1 to 8 carbon atoms in a straight or branched chain;

to obtain a compound of formula $Ie_1$:

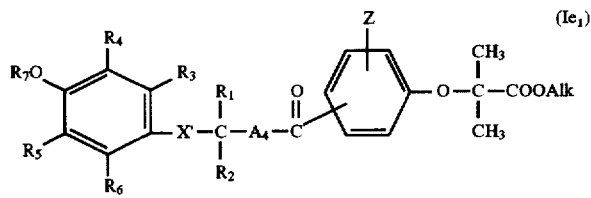

wherein $R_1$, $R_2$, $R_3$, $R_4$, $R_5$, $R_6$, $R_7$, $X'$, $A_4$, $Z$ and Alk are as defined above;

which compound of formula $Ie_1$ defined above may be saponified to give the corresponding acid of formula $Ie_2$:

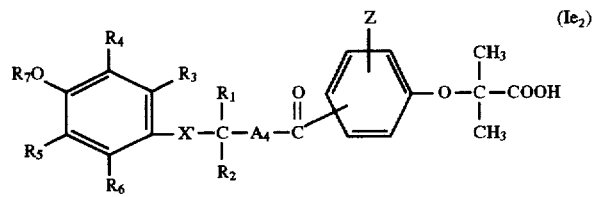

wherein $R_1$, $R_2$, $R_3$, $R_4$, $R_5$, $R_6$, $R_7$, $X'$, $A_4$ and $Z$ are as defined above; or f). the compound of formula $Ie_1$ defined above is reacted with a chemical reducing agent, such as, for example, sodium borohydride, or with hydrogen in the presence of a hydrogenation catalyst to obtain the compound of formula $If_1$:

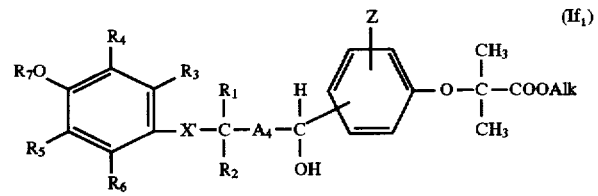

wherein:

$R_1$, $R_2$, $R_3$, $R_4$, $R_5$, $R_6$, $R_7$, $X'$, $Z$ and Alk are as defined above;

which compound of formula $If_1$ defined above may be saponified to give the corresponding acid of formula $If_2$:

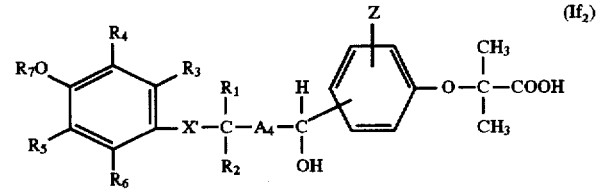

wherein $R_1$, $R_2$, $R_3$, $R_4$, $R_5$, $R_6$, $R_7$, $X'$, $A_4$ and $Z$ are as defined above; or g). a compound of formula $If_1$ defined above is reacted with a hydracid of formula IV:

H—Y   (IV)

wherein Y is as defined above.

to obtain a compound of formula $Ig_1$:

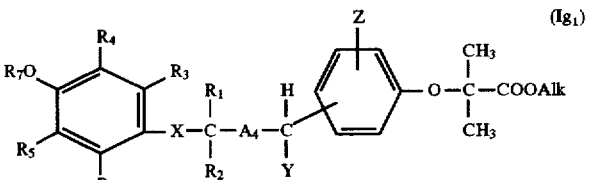

wherein $R_1$, $R_2$, $R_3$, $R_4$, $R_5$, $R_6$, $R_7$, $A_4$, Y, Z and Alk are as defined above, which compound $Ig_1$ defined above is hydrolysed to give the corresponding acid of formula $Ig_2$:

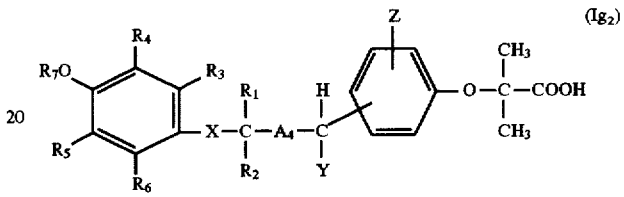

wherein $R_1$, $R_2$, $R_3$, $R_4$, $R_5$, $R_6$, $R_7$, $A_4$, Y and Z are as defined above.

The totality of the compounds of formulae $Ia_1$, $Ia_2$, $Ib_1$, $Ib_2$, $Ic_1$, $Ic_2$, $Ic_3$, $Id_1$, $Id_2$, $Ie_1$, $Ie_2$, $If_1$, $If_2$, $Ig_1$ and $Ig_2$ form the totality of the compounds of formula I.

It is especially advantageous to react the compounds of the respective formulae IIa and IIIa in the presence of an acceptor for the hydracid formed in the course of the reaction, in a solvent, such as, for example, acetone, acetonitrile or dimethylformamide, at a temperature of from 50° to 120° C.

There may be used as acceptor, for example, an alkali metal carbonate in the presence of an alkali metal iodide, dimethylaminopyridine or triethylamine.

The reaction of the compounds of the respective formulae IIb and IIIb is carried out in accordance with the technique of O. Mitsunobu, Synthesis (1981), 1–28, using ethyl azodicarboxylate and triphenylphosphine as reagents and operating in an aprotic solvent, such as, for example, tetrahydrofuran or ether, at a temperature of from 20° to 25° C.

The reaction of the compounds of the respective formulae IIc and IIIc is advantageously carried out in accordance with the technique of Wittig, G., Ann (1953), 580, 44 and Bruce et al., Chem. Rev. (1989), 863–927, using butyl lithium as reagent and operating in a tetrahydrofuran medium at a temperature of from 20° to 25° C.

A variant of that technique that gives greater yields is effected in accordance with Buddrus, Chem. Ber. (1974), 107, 2050–2061. In that case, the operation is carried out in the presence of 1,2-epoxybutane in excess, which serves both as reagent and solvent, at reflux temperature (63° C.).

The catalytic hydrogenation of the compound $Ic_1$ is effected by means of palladium-on-carbon under a pressure of $5.10^5$ Pa, operating in ethanol at a temperature of from 20° to 50° C.

The starting materials of formulae IIa and IIb are commercial products already described in the literature.

The starting materials of formula IIIb are obtained in the form of oils in accordance with the process that consists in reacting a compound of the formula:

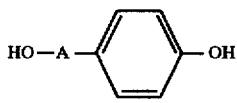

wherein A is as defined above, with an excess of a compound of the formula:

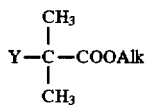

wherein Y and Alk are as defined above; the reaction being carried out in a suitable solvent, such as, for example, 3-methylpentanone, at a temperature of approximately 118° C. in the presence of an acceptor for the hydracid formed in the course of the reaction, such as, for example, potassium carbonate in the presence of potassium iodide.

The starting materials of formula IIIa are obtained in the form of oils by reacting the compounds of formula IIIb with triphenylphosphine in the presence of $CCl_4$ or of bromine in acetonitrile, in accordance with the method of J. Hooz et al., Can. J. Chem. 46, 86–87 (1968) and of J. Schaefer et al., Org. Synth. Coll. Vol. V, 249.

The starting materials of formula IIc are described in the literature and are prepared in accordance with N. Cohen et al., J. Am. Chem. Soc. 101, 6710–6715 (1979) or in accordance with Takeda, E.P. 345 593.

The starting materials of formula IIIc are prepared in non-crystallised amorphous form in accordance with the conventional process which consists in reacting a compound of formula IIIa such as defined above under reflux with triphenylphosphine in acetonitrile for 20 hours.

The starting materials of the respective formulae IId and IIId were prepared using customary reactions starting from the suitably protected corresponding phenols.

The starting materials of formula IIIe were prepared starting from commercial ketophenols by the usual conventional methods.

The reduction of the compound of formula $Ie_1$ by a chemical reducing agent may be carried out in a solvent, such as methanol, ethanol, dimethylformamide or tetrahydrofuran. The catalytic hydrogenation of the compound of formula $Ie_1$ may be effected using as catalyst palladium-on-carbon, palladium hydroxide-on-carbon, platinum-on-carbon or Raney nickel.

The compounds of formula I so obtained can be purified by flash chromatography on silica (35–70μ) using as eluant, for example, $H_3C$—$COOC_2H_5$ or $CH_2Cl_2/CH_3OH$, or by forming salts and crystallising those salts.

Some compounds of formula I give salts with physiologically tolerable bases, which salts, as such, are included in the present invention.

The compounds of the present invention possess valuable pharmacological and therapeutic properties.

In particular, it has been demonstrated in vitro and ex vivo that those compounds have the capacity to protect human LDL (low-density lipoproteins, which effect the transport of cholesterol) against oxidative modifications induced by copper and by endothelial cells.

Oxidative modifications in LDL appear at present to constitute an important mechanism in the formation and extension of atheromatous vascular lesions. Thus, the antioxidant properties, especially with respect to LDL, of the compounds of the present invention enable them to be used as medicaments in the treatment of:

hypercholesterolaemia, hypertriglyceridaemia, dyslipaemia and diabetes, in order to prevent complications, especially vascular complications, atherosclerosis in its various vascular, peripheral, coronary and cerebral manifestations, and also in pathologies in which membrane lipid peroxidation plays an initiating and/or aggravating role, such as ischaemic cardiopathy, reperfusion of organs, including transplanted organs, traumatic or degenerative ischaemic pathologies of the central or peripheral nervous system, acute or chronic inflammatory diseases and auto-immune diseases.

The present invention relates also to pharmaceutical compositions containing as active ingredient a compound of formula I or a physiologically tolerable salt thereof mixed or associated with a suitable pharmaceutical excipient, such as, for example, glucose, lactose, starch, talc, ethylcellulose, magnesium stearate or cocoa butter.

Those pharmaceutical compositions are generally presented in dosage form and may contain from 5 to 250 mg of active ingredient.

They may, for example, be in the form of tablets, dragées, gelatin capsules, suppositories or injectable or drinkable solutions, and may be administered orally, rectally or parenterally, as the case may be, at a dose of from 5 to 500 mg once or twice daily.

The following Examples illustrate the present invention, the melting points being determined using a Kofler hot block (K) or a capillary tube (cap).

EXAMPLE 1

2-{4-[2-(3,5-di-tert-butyl-4-hydroxyphenylthio) ethyl]phenoxy}isobutyric acid

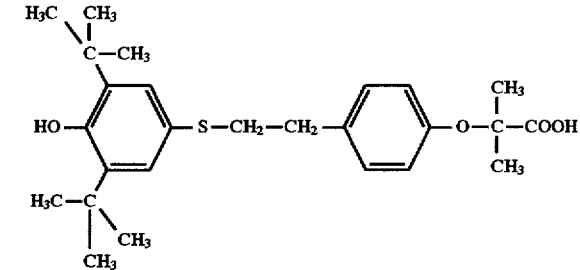

5.55 g (0.0176 mol) of ethyl 2-[4-(2-bromoethyl) phenoxy]isobutyrate, 4.25 g (0.025 mol) of 4-hydroxy-3,5-di-tert-butylphenylthiol, 2.43 g of sodium carbonate, 125 ml of acetone and 1 g of potassium iodide are introduced into a three-necked flask that is equipped with a stirrer and a condenser and is placed under a nitrogen atmosphere. The whole is heated to reflux temperature, which is maintained for 20 hours. It is then concentrated to dryness and the residue is taken up in methylene chloride and water.

After decanting, the organic phase is dried over sodium sulphate and concentrated to dryness and the residue is chromatographed on 700 cm³ of Amicon silica (0.035–0.070 mm), while eluting with a mixture of cyclohexane and methylene chloride (70:30).

The desired phases are concentrated to yield 7.8 g of the expected ester in the form of an oil. Yield 94%.

7.6 g (0.016 mol) of the ester obtained above, 300 ml of ethanol and 18 ml of 1N sodium hydroxide solution are introduced into a three-necked flask that is equipped with a stirrer and a condenser and is placed under a nitrogen atmosphere. The whole is heated under reflux for 12 hours and then concentrated to dryness.

The residue is taken up in a mixture of diethyl ether and water. The aqueous phase is extracted several times with diethyl ether. The combined ethereal phases are dried over sodium sulphate. Crystallisation is observed. The crystals are filtered off with suction and taken up in 100 ml of 1N hydrochloric acid and 200 ml of diethyl ether. The whole is stirred vigorously and decanted, and the organic phase is washed with a saturated sodium chloride solution, dried over sodium sulphate and concentrated to dryness.

The gummy residue is taken up in 30 ml of cyclohexane under reflux. The whole is cooled and crystallisation is observed. The crystals are filtered off with suction, washed with cold cyclohexane and dried at 60° C. under 67 Pa to yield 5.4 g of 2-{4-[2-(3,5-di-tert-butyl-4-hydroxyphenylthio)ethyl]phenoxy}isobutyric acid in the form of white crystals melting (K) at 100° C. Yield 76%.

EXAMPLES 2-8

By proceeding as described in Example 1, the compounds forming the subject of the following Examples were prepared:

2) ethyl 2-{4-[2-(4-hydroxy-2,3,5-trimethylphenylthio)ethyl]phenoxy}isobutyrate (gum).

3) 2-{4-[2-(4-hydroxy-2,3,5-trimethylphenylthio)ethyl]phenoxy}isobutyric acid, m.p. (K): 70° C. (ethyl acetate).

4) 2-[4-(3,5-di-tert-butyl-4-hydroxyphenylthiomethyl)phenoxy]isobutyric acid, m.p. (K): 134° C. (CH$_2$Cl$_2$/acetone).

5) the tert-butylamine salt of 2-{4-[3-(3,5-di-tert-butyl-4-hydroxyphenylthio)propyl]phenoxy}isobutyric acid, m.p. (K): 124° C. (petroleum ether).

6) the tert-butylamine salt of 2-{4-[5-(3,5-di-tert-butyl-4-hydroxyphenylthio)pentyl]phenoxy}isobutyric acid, m.p. (cap): 106°–110° C. (pentane).

7) sodium 2-{4-chloro-3-[2-(4-hydroxy-2,3,5-trimethylphenylthio)ethyl]phenoxy}isobutyrate (lyophilisate).

8) 2-{4-chloro-3-[2-(3,5-di-tert-butyl-4-hydroxyphenylthio)ethyl]phenoxy}isobutyric acid, m.p. (cap): 104°–107° C.

EXAMPLE 9

2-{4-[2-(4-hydroxy-2,3,5-trimethylphenoxy)ethyl]Phenoxy}isobutyric acid

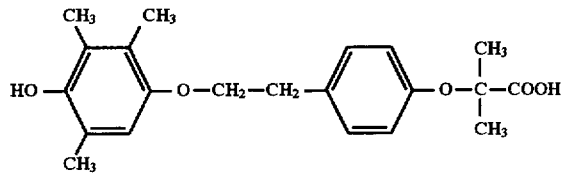

11 g (0.0567 mol) of 4-acetoxy-2,3,5-trimethylphenol, melting (K) at 108° C., 16.3 g of triphenylphosphine and 300 ml of tetrahyrofuran are introduced into a three-necked flask that is equipped with a stirrer, a condenser, a dropping funnel and a thermometer and is placed under a nitrogen atmosphere. The whole is cooled to 5° C. and 10.65 g of ethyl azodicarboxylate in solution in 75 ml of tetrahydrofuran are introduced over a period of 15 minutes, with stirring and while keeping the temperature below 10° C. The whole is stirred for 30 minutes at 5° C. and 15.5 g of ethyl 2-[4-(2-hydroxyethyl)phenoxy]isobutyrate in solution in 100 ml of tetrahydrofuran are introduced without the temperature exceeding 5° C. The whole is stirred for 1 hour at 5° C. and then for 20 hours at ambient temperature and then concentrated to dryness. The residue is triturated in cyclohexane and filtered, and the filtrate is concentrated to dryness.

The concentrate is chromatographed on 2.7 liters of Amicon silica (0.035–0.070 mm) while eluting with methylene chloride. The desired fractions are concentrated to yield 10.7 g of the expected ester in the form of a gum. Yield: 44%.

10.5 g (0.0245 mol) of the ethyl 2-{4-[2-(4-acetoxy-2,3,5-trimethylphenoxy)ethyl]phenoxy}isobutyrate so obtained are introduced with 500 ml of ethanol and 50 ml of 1N sodium hydroxide solution into a three-necked flask that is equipped with a stirrer and a condenser and is placed under a nitrogen atmosphere. The whole is heated under reflux for 3 hours and then concentrated to dryness. The residue is taken up in water and extracted several times with ether. The aqueous phase is acidified with 55 cm$^3$ of 1N hydrochloric acid and then extracted several times with ether. The combined ethereal phases are washed with water, dried over sodium sulphate and concentrated to dryness. The residue is chromatographed on 1.4 liters of Amicon silica (0.035–0.070 mm) while eluting with a mixture of methylene chloride and ethyl acetate (70:30). The desired fractions are concentrated to dryness. The residue is dissolved in 20 ml of ether. The whole is diluted with petroleum ether and cooled. Crystallisation is observed. The crystals are filtered off with suction and dried at 45° C. under 133 Pa to yield 6 g of 2-{4-[2-(4-hydroxy-2,3,5-trimethylphenoxy)ethyl]phenoxy}isobutyric acid in the form of white crystals melting (K) at 69° C. Yield: 68%.

EXAMPLES 10-14

By proceeding as described in Example 9, the compounds forming the subject of the following Examples were prepared:

10) 2-{4-[2-(3,5-di-tert-butyl-4-hydroxyphenoxy)ethyl]phenoxy}isobutyric acid, m.p. (cap): 119°–120° C. (CH$_2$Cl$_2$/acetone).

11) the tert-butylamine salt of 2-{4-[5-(3,5-di-tert-butyl-4-hydroxyphenoxy)pentyl]phenoxy}isobutyric acid, m.p. (cap): 132°–133° C. (pentane).

12) ethyl 2-{4-[2-(4-acetoxy-2,3,5-trimethylphenoxy)ethyl]phenoxy}isobutyrate (gum).

13) sodium 2-{4-chloro-3-[2-(4-hydroxy-2,3,5-trimethylphenoxy)ethyl]phenoxy}isobutyrate (lyophilisate).

14) tert-butylamine 2-{4-chloro-3-[2-(3,5-di-tert-butyl-4-hydroxyphenoxy)ethyl]phenoxy}isobutyrate, m.p. (cap): 160°–163° C. (ether/petroleum ether).

EXAMPLE 15

Tert-butylamine (Z)-(R,S)-2-{4-[3-(6-hydroxy-2,5,7,8-tetramethylchroman-2-yl)prop-2-en-1-yl]phenoxy}isobutyrate

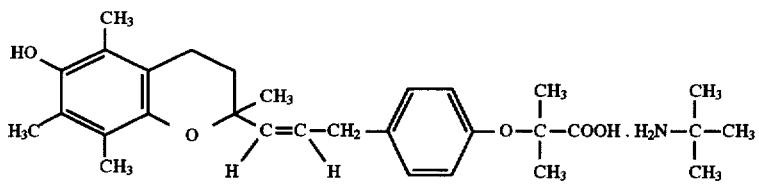

30 g (0.052 mol) of 2-{4-[2-(ethoxycarbonyl)propan-2-yloxy]phenyl}ethyltriphenylphosphonium bromide, 15.2 g (0.052 mol) of 6-ethoxymethoxy-2-formyl-2,5,7,8-tetramethylchroman, melting (K) at 66° C., and 1.8 liters of 1,2-epoxybutane are introduced into a round-bottomed flask equipped with a stirrer and a condenser. The whole is heated under reflux for 48 hours and then concentrated to dryness. The residue is taken up in toluene and concentrated again.

The residue is chromatographed on 2 liters of Amicon silica (0.035–0.070 mm) while eluting with a mixture of chloroform (stabilised with amylene) and ethyl acetate (96:4). The desired fractions are concentrated to dryness to yield 21.2 g of ethyl (Z)-(R,S)-2-{4-[3-(6-ethoxymethoxy-2,5,7,8-tetramethylchroman-2-yl)prop-2-en-1-yl]phenoxy}isobutyrate in the form of a gum. Yield 80%.

The 6-ethoxymethoxy-2-formyl-1,2,5,7,8-tetramethylchroman used as starting material was prepared by reducing the corresponding methyl ester (oil, $n_D^{20°\ C}$: 1.5207) using diisobutylaluminium hydride, which methyl ester was itself prepared from the methyl ester of Trolox and chloromethyl ethyl ether in dimethylformamide in the presence of NaH.

5.1 g (0.01 mol) of the ethyl (Z)-(R,S)-2-{4-[3-(6-ethoxymethoxy-2,5,7,8-tetramethylchroman-2-yl)prop-2-en-1-yl]phenoxy}isobutyrate prepared above, 100 ml of ethanol and 20 ml of 1N hydrochloric acid are introduced into a round-bottomed flask equipped with a stirrer and a condenser. The whole is heated under reflux for 3 hours and left to stand overnight at ambient temperature. It is then concentrated to dryness and the residue is taken up in diethyl ether, washed with a saturated sodium chloride solution, dried over sodium sulphate and concentrated to dryness. The residue is taken up in 200 ml of ethanol to which 20 ml of 1N sodium hydroxide solution are added. The whole is left to stand for 20 hours at ambient temperature and then concentrated to dryness. The residue is taken up in 21 ml of 1N HCl. Extraction is carried out several times with diethyl ether. The ethereal phases are washed with a saturated sodium chloride solution and then dried over sodium sulphate. The whole is concentrated to dryness. The residue is chromatographed on 500 ml of Amicon silica (0.035–0.070 mm) while eluting with a mixture of $CH_2Cl_2$ and acetone (90:10). The desired fractions are concentrated to dryness. The residue is dissolved in 20 ml of diethyl ether. 0.5 g of tert-butylamine is added. The whole is concentrated to dryness and the residue is triturated in petroleum ether. Crystallisation is observed. The crystals are filtered off with suction, washed with petroleum ether and dried at 50° C. under 133 Pa to yield 2.7 g of tert-butylamine (Z)-(R,S)-2-{4-[3-(6-hydroxy-2,5,7,8-tetramethylchroman-2-yl)prop-2-en-1-yl]phenoxy}isobutyrate, m.p. (cap): 125°–128° C. Yield: 63%.

EXAMPLES 16–17

By proceeding as described in Example 15, the compounds forming the subject of the following Examples were prepared:

16) (Z)-2-{4-[3-(3,5-di-tert-butyl-4-hydroxyphenyl)prop-2-en-1-yl]phenoxy}isobutyric acid, m.p. (cap): 111°–114° C. (petroleum ether).

17) sodium (Z)-(R,S)-2-{4-[6-(6-hydroxy-2,5,7,8-tetramethylchroman-2-yl)hex-5-en-1-yl]phenoxy}isobutyrate (lyophilisate).

EXAMPLE 18

Tert-butylamine (R,S)-2-{4-[3-(6-hydroxy-2,5,7,8-tetra-methylchroman-2-yl)propyl]phenoxy}isobutyrate

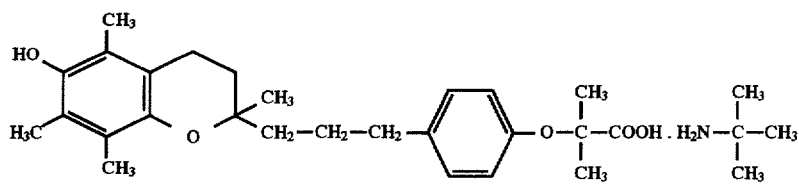

4.05 g (0.079 mol) of ethyl (Z)-(R,S)-2-{4-[3-(6-ethoxymethoxy-2,5,7,8-tetramethylchroman-2-yl)prop-2-en-1-yl]phenoxy}isobutyrate, 80 ml of ethanol and 0.45 g of palladium-on-carbon are introduced into a Parr hydrogenating apparatus. Hydrogenation is carried out for 20 hours under a pressure of $5.10^5$ Pa at 50° C. The whole is filtered and concentrated to dryness. The residue is chromatographed on 170 cm³ of Amicon silica (0.035– 0.070 mm) while eluting with a mixture of toluene and ethyl acetate (96:4). The desired fractions are concentrated to dryness to yield 2.7 g of ethyl (R,S)-2-{4-[3-(6-ethoxymethoxy-2,5,7,8-tetramethylchroman-2-yl)propyl]phenoxy}isobutyrate in the form of a gum.

6.0 g (0.012 mol) of the ethyl (R,S)-2-{4-[3-(6-ethoxymethoxy-2,5,7,8-tetramethylchroman-2-yl)propyl]phenoxy}isobutyrate obtained above, 100 ml of ethanol and 20 ml of 1N HCl are introduced into a round-bottomed flask equipped with a stirrer and a condenser. The whole is heated under reflux for 3 hours and then concentrated to dryness. The residue is taken up in diethyl ether, washed with a saturated sodium chloride solution, dried over sodium sulphate and concentrated to dryness. The residue is taken up in 250 ml of ethanol. 25 ml of 1N sodium hydroxide solution are added and the whole is left to stand overnight at ambient temperature. It is then neutralised with 25 ml of 1N HCl and concentrated to dryness. The residue is taken up in diethyl ether, washed with a saturated sodium chloride solution, dried over sodium sulphate and concentrated to dryness.

The residue is chromatographed on 450 cm³ of Amicon silica (0.035–0.070 mm) while eluting with a mixture of toluene and acetone (95:5). The desired fractions are concentrated at a temperature below 45° C. The residue is dissolved in 20 ml of ether.

0.35 g of tert-butylamine is added. Dilution is carried out gradually with 80 ml of petroleum ether. The whole is left to stand overnight in a refrigerator, the crystals are filtered off with suction, washed with petroleum ether and dried at 40° C. under 133 Pa to yield 1.4 g of tert-butylamine (R.S)-2-{4-[3-(6-hydroxy-2,5,7,8-tetramethylchroman-2-yl)propyl]phenoxy}isobutylrate, m.p. (cap): 115°–118° C. Yield: 23%.

EXAMPLES 19–22

By proceeding as described in Example 18, the compounds forming the subject of the following Examples were prepared:

19) sodium (R,S)-2-{4-[6-(6-hydroxy-2,5,7,8-tetramethylchroman-2-yl)hexyl]phenoxy}-2-methylpropionate (lyophilisate).
20) 2-{4-[3-(3,5-di-tert-butyl-4-hydroxyphenyl)propyl]phenoxy}isobutyric acid, m.p. (cap): 82°–83° C. (diethyl ether).
21) sodium 2-{4-chloro-3-[2-(3,5-di-tert-butyl-4-hydroxyphenyl)propyl]phenoxy}isobutyrate (lyophilisate).
22) sodium (R,S)-2-{4-chloro-3-[3-(6-hydroxy-2,5,7,8-tetramethyl-3,4-dihydrobenzopyran-2-yl)propyl]phenoxy}isobutyrate (lyophilisate).

EXAMPLE 23

Tert-butylamine 2-{4-[2-(4-hydroxy-3,5-di-tert-butylphenylthio)ethoxy]phenoxy}isobutyrate

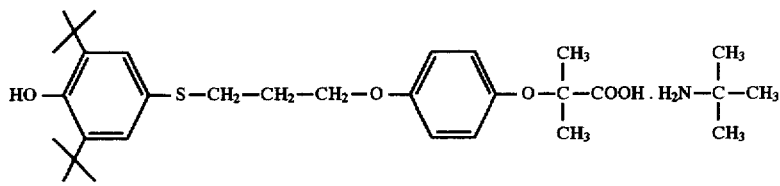

6.7 g (0.03 mol) of ethyl 2-(4-hydroxyphenoxy)isobutyrate, 10.2 g (0.03 mol) of 2-(4-ethoxymethoxy-3,5-di-tert-butylphenylthio)ethanol, 7.9 g (0.03 mol) of triphenylphosphine and 160 ml of tetrahydrofuran are introduced into a three-necked flask equipped with a stirrer, a condenser and a dropping funnel.

The whole is cooled to 5° C. and 5.2 g of diethyl azodicarboxylate dissolved in 40 ml of tetrahydrofuran are introduced over a period of one hour. Stirring is maintained for 7 hours at ambient temperature, and then the whole is cooled to 5° C. and 7.9 g (0.03 mol) of triphenylphosphine are added again followed by 5.2 g (0.03 mol) of diethyl azodicarboxylate. The whole is stirred for 16 hours at ambient temperature and then concentrated to dryness at a temperature below 35° C. Cyclohexane is added and trituration is carried out until crystallisation is observed. The whole is filtered and the filtrate is concentrated to dryness. The residue is chromatographed on 2 liters of Amicon silica/0.035–0.07 mm while eluting with a mixture of dichloromethane and cyclohexane (70:30). The fractions retained are concentrated to dryness to yield 4.5 g of ethyl 2-{4-[2-(4-ethoxymethoxy-3,5-di-tert-butylphenylthio)ethoxy]phenoxy}isobutyrate (yield: 27%) in the form of a gum.

4.47 g of the ethyl 2-(4-[2-{4-ethoxymethoxy-3,5-di-tert-butylphenylthio)ethoxy]phenoxy}isobutyrate obtained above, 70 ml of ethanol and 11 ml of 1N sodium hydroxide solution are introduced into a 250 ml three-necked flask equipped with a stirrer and a condenser.

The whole is heated under reflux for 16 hours and then cooled, neutralised with 11 ml of 1N HCl and concentrated to dryness. The residue is taken up in ether, washed with water, dried over sodium sulphate and concentrated to dryness. The residue is chromatographed on 120 g of silica while eluting first with dichloromethane and then with a mixture of dichloromethane and acetone (95:5). The fractions retained are concentrated to dryness to yield 4.0 g of 2-{4-[2-(4-ethoxymethoxy-3,5-di-tert-butylphenylthio)ethoxy]phenoxy}isobutyric acid in the form of a gum (yield: 95%).

3.8 g (0.0073 mol) of the 2-{4-[2-(4-ethoxymethoxy-3,5-di-tert-butylphenylthio)ethoxy]phenoxy}isobutyric acid obtained above and 60 ml of 4N hydrochloric acid in dioxane are introduced into a 250 ml round-bottomed flask. The whole is left to stand for 20 hours at ambient temperature. A current of nitrogen is passed through into order to remove some of the excess hydrochloric acid. The whole is concentrated to dryness without heating and then the residue is taken up in ether, washed several times with water, dried over sodium sulphate and concentrated to dryness. The residue is chromatographed on 300 ml of Amicon silica (0.035–0.07 mm) while eluting first with dichloromethane and then with a mixture of dichloromethane and acetone (90:10). The fractions retained are concentrated to dryness to yield 2.9 g of a gum which is dissolved in 30 ml of cyclohexane. 0.45 g of tert-butylamine dissolved in 20 ml of cyclohexane is added and the whole is dried at 50° C. under 0.5 torr to yield 2.8 g of tert-butylamine 2-{4-[2-(4-hydroxy-3,5-di-tert-butylphenylthio)ethoxy]phenoxy}isobutyrate melting (cap) at 157°–159° C. (yield: 72%).

EXAMPLE 24

Ethyl 2-{4-[2-(3,5-di-tert-butyl-4-hydroxyphenylthio)-1-oxoethyl]phenoxy}isobutyrate

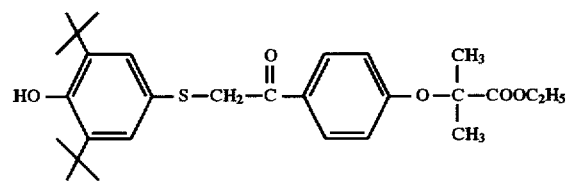

9.6 g (0.04 mol) of 4-hydroxy-3,5-di-tert-butylphenylthiol, 13.2 g of ethyl 2-(4-bromoacetylphenoxy)

isobutyrate, 5.6 g of potassium carbonate and 180 ml of acetone are introduced into a three-necked flask equipped with a stirrer and a condenser. The whole is stirred for 3 days at ambient temperature and then filtered and concentrated to dryness. The residue is taken up in dichloromethane. The solution is washed with a 10% aqueous sodium hydrogen carbonate solution. The whole is dried over sodium sulphate and concentrated to dryness. The residue is chromatographed on 2 liters of Amicon silica (0.035–0.070 mm) while eluting with a mixture of dichloromethane and cyclohexane (50:50). The fractions retained are concentrated to dryness to yield 15.74 g of ethyl 2-{4-[1-oxo-2-(4-hydroxy-3,5-di-tert-butylphenylthio)ethyl]phenoxy}isobutyrate in the form of a non-crystallised gum (yield: 81%).

The ethyl 2-(4-bromoacetylphenoxy)isobutyrate used as starting material was prepared as follows: 10 g (0.04 mol) of ethyl 2-(4-acetylphenoxy)isobutyrate and 100 ml of tetrahydrofuran are introduced into a three-necked flask equipped with a stirrer. 19.9 g of pyrrolidone hydrobromide dissolved in 400 ml of tetrahydrofuran are added over a period of 1 hour at a temperature below 25° C. The whole is stirred for 20 hours at ambient temperature and then filtered and concentrated to dryness without the temperature exceeding 40° C. The residue is taken up in dichloromethane, washed with a 10% sodium hydrogen carbonate solution, dried over sodium sulphate and concentrated to dryness. The residue is chromatographed on 1.2 liters of Amicon silica (0.035–0.070 mm) while eluting with a mixture of dichloromethane and cyclohexane (80:20). The fractions retained are concentrated to dryness to yield 7.85 g of ethyl 4-(2-bromoacetylphenoxy)isobutyrate in the form of a thick liquid (yield: 60%).

The ethyl 2-(4-acetylphenoxy)isobutyrate used as starting material was itself prepared as follows: 54.4 g of 4-hydroxyacetophenone, 375 ml of ethyl 2-bromoisobutyrate, 175 g of potassium carbonate, 1.2 liters of methyl isobutyl ketone and 3 g of potassium iodide are introduced into a three-necked flask equipped with a stirrer and a condenser. The whole is heated under reflux for 20 hours, then cooled, filtered and concentrated to dryness. The residue is chromatographed on 4 liters of Amicon silica (0.035–0.070 mm) while eluting with dichloromethane. The fractions retained are concentrated to dryness to yield 100 g of ethyl 2-(4-acetylphenoxy)isobutyrate in the form of a thick liquid (quantitative yield).

EXAMPLE 25

By proceeding analogously to Example 24, the following compound was prepared:
ethyl 2-{4-[2-(3,5-di-tert-butyl-4-hydroxyphenyl)-1-oxoethyl]phenoxy}isobutyrate, m.p. (K): 117° C. (cyclohexane).

EXAMPLE 26

2-{4-[2-(3,5-di-tert-butyl-4-hydroxyphenylthio)-1-oxoethyl]phenoxy}isobutyric acid

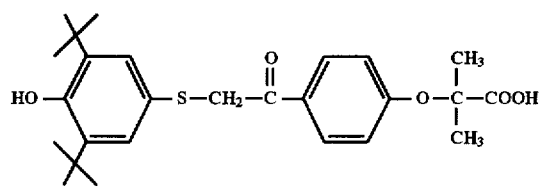

4.86 g (0.01 mol) of ethyl 2-{4-[1-oxo-2-(4-hydroxy-3,5-di-tert-butylphenylthio)ethyl]phenoxy}isobutyrate, 70 ml of ethanol and 12 ml of 1N sodium hydroxide solution are introduced into a round-bottomed flask equipped with a magnetic stirrer. The whole is heated under reflux for 1 hour 30 minutes, then cooled, neutralised with 12 ml of 1N hydrochloric acid solution and concentrated to dryness. The residue is taken up in ether. The whole is washed with water, dried over sodium sulphate and concentrated to dryness. The residue is chromatographed on 300 ml of Amicon silica (0.035–0.070 mm) while eluting first with pure dichloromethane and then with a mixture of dichloromethane and methanol (97:3).

The fractions retained are concentrated to dryness. The residue is triturated in petroleum ether and dried at a temperature below 40° C. to yield 1.5 g of 2-{4-[2-(3,5-di-tert-butyl-4-hydroxyphenoxythio)ethyl]phenoxy}isobutyric acid, m.p. (K): 141° C. (yield: 33%).

EXAMPLE 27

By proceeding analogously to Example 26, the following compound was prepared:

tert-butylamine 2-{4-[2-(3,5-di-tert-butyl-4-hydroxyphenoxy)-1-oxoethyl]phenoxy}isobutyrate, m.p. (cap): 162°–165° C.

EXAMPLE 28

Tert-butylamine (R,S)-2-{4-[2-(3,5-di-tert-butyl-4-hydroxyphenylthio)-1-hydroxyethyl]phenoxy}isobutyrate

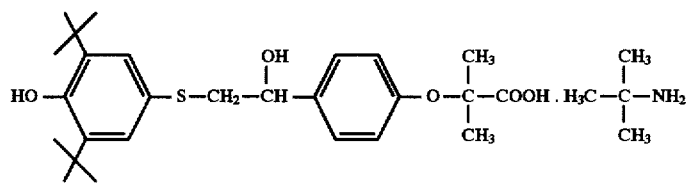

4.86 g (0.01 mol) of ethyl 2-{4-[1-oxo-2-(4-hydroxy-3,5-di-tert-butylphenylthio)ethyl]phenoxy}isobutyrate and 50 ml of tetrahydrofuran are introduced into a 250 ml three-necked flask equipped with a stirrer and a dropping funnel. At 5° C., 0.5 g of sodium borohydride and then 3.5 ml of water are added. The whole is stirred for 1 hour at ambient temperature and then cooled to 5° C. and 0.5 g of sodium borohydride is again added. The whole is stirred for 4 hours at ambient temperature, then concentrated to dryness at a temperature below 40° C. The residue is taken up in dichloromethane and washed with a 10% sodium hydrogen carbonate solution. The whole is dried over sodium sulphate and concentrated to dryness. The residue is chromatographed on 400 ml of Amicon silica (0.035–0.070 mm) while eluting with dichloromethane. The fractions retained are concentrated to dryness to yield 4.2 g of ethyl (R,S)-2-{4-[1-hydroxy-2-(4-hydroxy-3,5-di-tert-butylphenylthio)ethyl]phenoxy}isobutyrate (yield: 86%) in the form of a gum.

The product is taken up in 84 ml of ethanol. 10 ml of 1N sodium hydroxide solution are added and the whole is left to stand for 72 hours at ambient temperature. 11 ml of 1N hydrochloric acid are added and the whole is concentrated to dryness at a temperature below 35° C. The residue is taken up in diethyl ether. The whole is washed with water, dried over sodium sulphate and concentrated to dryness. The residue is chromatographed on Amicon silica (0.035–0.070 mm) while eluting first with dichloromethane and then with a mixture of dichloromethane and acetone (97:3). The fractions retained are concentrated to dryness. The residue is taken up in water. 0.35 g of tert-butylamine is added. The aqueous solution is extracted with petroleum ether and then lyophilised to yield 1.8 g of tert-butylamine (R,S)-2-{4-[1-hydroxy-2-(4-hydroxy-3,5-di-tert-butylphenylthio)ethyl]phenoxy}isobutyrate in the form of a lyophilisate (yield: 39%).

4.8 g of the ethyl 2-{4-[2-(4-ethoxymethoxy-3,5-di-tertbutylphenoxy)ethoxy]phenoxy})isobutyrate obtained above, 70 ml of ethanol and 12 ml of 1N sodium hydroxide solution are introduced into a 250 ml three-necked flask equipped with a stirrer and a condenser. The whole is heated under reflux for 16 hours, cooled, neutralised with 12.2 ml of 1N HCl and then concentrated to dryness. The residue is taken up in diethyl ether, washed with water, dried over sodium sulphate and concentrated to dryness. The residue is chromatographed on 300 ml of Amicon silica (0.035–0.070 mm) while eluting first with pure dichloromethane and then with a mixture of dichloromethane and acetone (85:15). The fractions retained are concentrated to dryness to yield 4.25 g of 2-{4-[2-(4-ethoxymethoxy-3,5-di-tert-butylphenoxy)ethoxy]phenoxy}isobutyric acid in the form of a gum (yield: 94%).

4 g of the acid obtained above and 60 ml of 4N hydrochloric acid in dioxane are introduced into a 250 ml round-bottomed flask. The whole is left to stand for 24 hours at ambient temperature. A current of nitrogen is passed though into order to remove some of the excess hydrochloric acid. The whole is concentrated to dryness at a temperature below 35° C. The residue is taken up in diethyl ether, washed with water, dried over sodium sulphate and concentrated to dryness at a temperature below 35° C. The residue is chromatographed on 120 g of Amicon silica (0.035–0.070 mm) while eluting first with pure dichloromethane and then with a mixture of dichloromethane and acetone (90:10). The fractions retained are concentrated to dryness to yield 2.85 g of 2-{4-[2-(4-hydroxy-3,5-di-tert-butylphenoxy)ethoxy]phenoxy}isobutyric acid which melts at 124° C. (yield: 81%).

EXAMPLE 29

2-{4-[2-(4-hydroxy-3,5-di-tert-butylphenoxy)ethoxy]phenoxy}isobutyric acid:

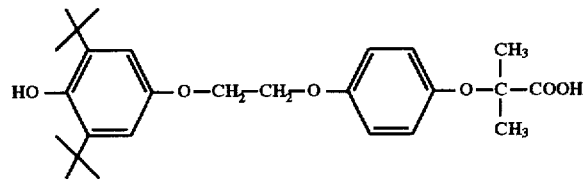

6.6 g (0.0293 mol) of ethyl 2-(4-hydroxyphenoxy)isobutyrate, 7.7 g of triphenylphosphine and 160 ml of tetrahydrofuran are introduced into a three-necked flask equipped with a stirrer, a condenser and a dropping funnel. The whole is cooled to 5° C. and 5.1 g of diethyl azodicarboxylate dissolved in 40 ml of tetrahydrofuran are introduced at a temperature below 10° C. The whole is stirred for 1 hour at 5° C. and then 9.5 g of 2-(4-ethoxymethoxy-3,5-di-tert-butylphenoxy)ethanol dissolved in 50 ml of tetrahydrofuran are added. The whole is stirred for 1 hour at 5° C. and then for 20 hours at ambient temperature and is subsequently concentrated to dryness at a temperature below 30° C. The residue is triturated in cyclohexane and filtered. The filtrate is concentrated to dryness and then chromatographed on 2.9 liters of Amicon silica (0.035–0.070 mm) while eluting with a mixture of dichloromethane and cyclohexane (80:20). The fractions retained are concentrated to dryness. Ethyl 2-{4-[2-(4-ethoxymethoxy-3,5-di-tert-butylphenoxy)ethoxy]phenoxy}isobutyrate crystallises, m.p. (K): 74° C. (yield: 31%).

EXAMPLE 30

Ethyl (R,S)-2-{4-[1-chloro-2-(3,5-di-tert-butyl-4-hydroxyphenoxy)ethyl]phenoxy}isobutyrate

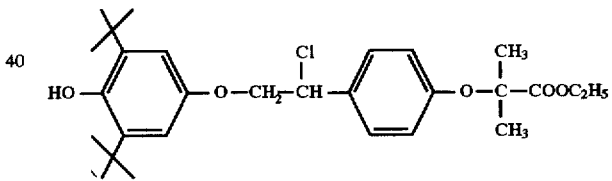

5.8 g (0.011 mol) of ethyl 2-{4-[1-oxo-2-(4-ethoxymethoxy-3,5-di-tert-butylphenoxy)ethyl]phenoxy}isobutyrate and 58 ml of tetrahydrofuran are introduced into a three-necked flask equipped with a stirrer. The whole is cooled to 5° C. and then 0.417 g of sodium borohydride and 3 ml of water are added. The whole is stirred for 2 hours at 5° C. and then for 20 hours at ambient temperature and subsequently concentrated to dryness at a temperature below 30° C. The residue is taken up in dichloromethane, washed with a 10% sodium hydrogen carbonate solution, dried over sodium sulphate and concentrated to dryness. The residue is chromatographed on 450 ml of Amicon silica (0.035–0.070 mm) while eluting first with pure dichloromethane and then with a mixture of dichloromethane and ethyl acetate. The fractions retained are concentrated to dryness to yield 3.6 g of ethyl (R,S)-2-{4-[1-hydroxy-2-(4-hydroxy-3,5-di-tert-butylphenoxy)ethyl]phenoxy}isobutyrate in the form of a gum (yield: 62%).

6.2 g of the hydroxy ester prepared above (0.0117 mol) and 100 ml of 4N hydrochloric acid in dioxane are introduced into a 500 ml round-bottomed flask. The whole is left to stand for 24 hours at ambient temperature. A current of nitrogen is passed through in order to remove some of the excess hydrochloric acid and then the whole is concentrated to dryness at a temperature below 30° C. The residue is taken up in ether, washed with a saturated sodium chloride solution, washed with water, dried over sodium sulphate and concentrated to dryness. The residue is chromatographed on 450 ml of silica while eluting with a mixture of dichloromethane and cyclohexane. The fractions retained are concentrated to dryness and the residue is triturated in petroleum ether. The crystals are filtered off with suction and dried at 50° C. under 0.5 torr to yield 2.5 g of ethyl (R,S)-2-{4-[1-chloro-2-(4-hydroxy-3,5-di-tert-butylphenoxy)ethyl]phenoxy}isobutyrate, m.p. (cap): 80°–81° C. (yield=43%).

EXAMPLE 31

PHARMACOLOGICAL STUDY

The action of the compounds of the present invention was demonstrated on human and animal LDL. The inhibitory activity of the compounds with respect to the oxidative modification of the LDL induced by copper sulphate and by endothelial cells from the rabbit aorta was demonstrated both in vitro (on human LDL) and after oral administration to Watanabe rabbits. The activity of the compounds was tested in comparison with probucol and vitamin E taken as reference products.

1. IN VITRO STUDY

1.1 Material and methods

1.1.1 Modification of LDL by copper sulphate

Human LDL are incubated for 24 hours in the presence of copper sulphate ($5.10^{-6}M$) and in the absence or in the presence of the test compounds ($10^{-9}M$ to $10^{-4}M$).

After incubation, the peroxidation of the LDL is evaluated by agar gel electrophoresis and by the formation of one of the products of lipid peroxidation: malonic dialdehyde (MDA) (Parthasarathy S., Young S. G., Witztum J. L., Pittman R. C., and Steinberg D.; J. Clin. Invest. 77; 641–644, 1986).

The activity of the test compounds is evaluated by calculating the concentrations that reduce by 50% (IC50) the production of MDA compared with the control experiments without those compounds.

1.1.2 Modification of LDL by endothelial cells

Human LDL are incubated for 24 hours in the presence of endothelial cells from the rabbit aorta (RECL B4 line provided by Professor Steinberg, U.S.A.), and in the absence or in the presence of the test compounds ($10^{-9}M$ to $10^{-4}M$).

After incubation, the peroxidation of the LDL is evaluated by agar gel electrophoresis and by the formation of one of the products of lipid peroxidation: malonic dialdehyde (MDA) (Steinbrecher U. P., Parthasarathy S., Leake D. S., Witztum J. L., and Steinberg D.; Proc. Nat. Acad. Sci. U.S.A. 81, 3883–3887, 1984).

The activity of the test compounds is evaluated by calculating the concentrations that reduce by 50% (IC50) the production of MDA compared with the control experiments without those compounds.

1.2 Results

1.2.1 Effect on LDL modification

Table A gives the IC50s, demonstrating the inhibitory activity on lipid peroxidation of human LDL, obtained with a sample of the compounds of the invention and with the reference products: probucol and vitamin E, in two tests relating to the inhibition of LDL oxidation induced by copper sulphate ($Cu^{2+}$) or by endothelial cells (EC).

TABLE A

| COMPOUNDS | IC50 (M) | |
|---|---|---|
| | $Cu^{2+}$ | EC |
| Example 1 | $5 \cdot 10^{-8}$ | $3 \cdot 10^{-9}$ |
| Example 3 | $9 \cdot 10^{-8}$ | |
| Example 4 | $3 \cdot 10^{-8}$ | |
| Example 5 | $4 \cdot 10^{-8}$ | |
| Example 9 | $5 \cdot 10^{-7}$ | |
| Example 10 | $2 \cdot 10^{-8}$ | $7 \cdot 10^{-9}$ |
| Example 15 | $4 \cdot 10^{-8}$ | |
| Example 18 | $6 \cdot 10^{-8}$ | |
| PROBUCOL | $3 \cdot 10^{-6}$ | $4 \cdot 10^{-6}$ |
| VITAMIN E | $>10^{-4}$ | $4 \cdot 10^{-6}$ |

The results clearly indicate the greater activity, especially of the compounds of Examples 1, 3, 4 and 5 compared with probucol or vitamin E, in protecting human LDL against modifications induced by copper sulphate and endothelial cells.

Those compounds, the IC50s of which with respect to peroxidation induced by copper sulphate ($5.10^{-6}M$) are from $2.10^{-8}$ to $5.10^{-7}$ are 100 times more effective than is probucol in this test; with regard to the test using endothelial cells, the compound of Example 1, with an IC50 of $3.10^{-9}M$, is found to be 1000 times more effective than is probucol.

Figure 2:
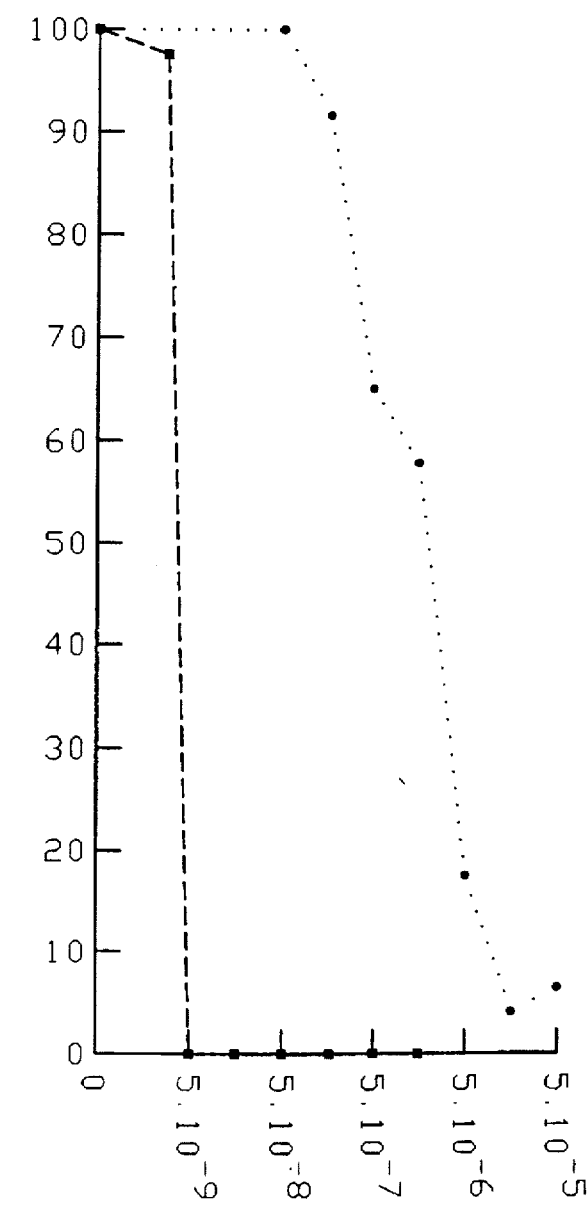
FIG. 2 shows peroxidation of LDL by endothelial cells and compares the effect of the compound of Example 1 with the effect of probucol.

By way of example, the effects of the compound of Example 1 have been illustrated by FIGS. 1 and 2.

2. EX VIVO STUDY

2.1 Materials and methods

Watanabe rabbits (genetically hyperlipidaemic rabbits) weighing from 3 kg to 5 kg are used. The animals are treated orally either with the excipient used for the test compounds (control group) or with the test products at a dose of 50 mg/kg/day for 3 days.

After treatment, the LDL of the animals are prepared by ultracentrifugation and subjected to oxidation with copper sulphate ($5.10^{-6}M$). The lipid peroxidation of the LDL is evaluated after various periods of incubation with copper sulphate (from 2 to 24 hours) by measuring the formation of MDA.

2.2 Results

Table B groups the MDA production values according to the period of incubation with copper sulphate of the LDL originating from control animals and from animals treated with the compound of Example 1 at different doses or with probucol.

TABLE B

| COMPOUNDS | NUMBER OF ANIMALS | MDA production (nmol/mg proteins) Period of incubation of the LDL with copper sulphate (hours) | | | | |
|---|---|---|---|---|---|---|
| | | 2 | 4 | 6 | 8 | 24 |
| Control | 6 | 3.31 ± 0.41 | 4.84 ± 0.59 | 13.41 ± 2.29 | 26.04 ± 2.82 | 28.06 ± 2.87 |
| Example 1 50 mg/kg/day | 4 | 0.66 ± 0.31 | 0.35 ± 0.35 | 0.31 ± 0.18 | 0.26 ± 0.26 | 0.86 ± 0.32 |
| Probucol 250 mg/kg/day | 5 | 1.85 ± 0.27 | 3.50 ± 0.27 | 4.90 ± 0.89 | 12.26 ± 2.45 | 23.81 ± 0.37 |

Figure 3:
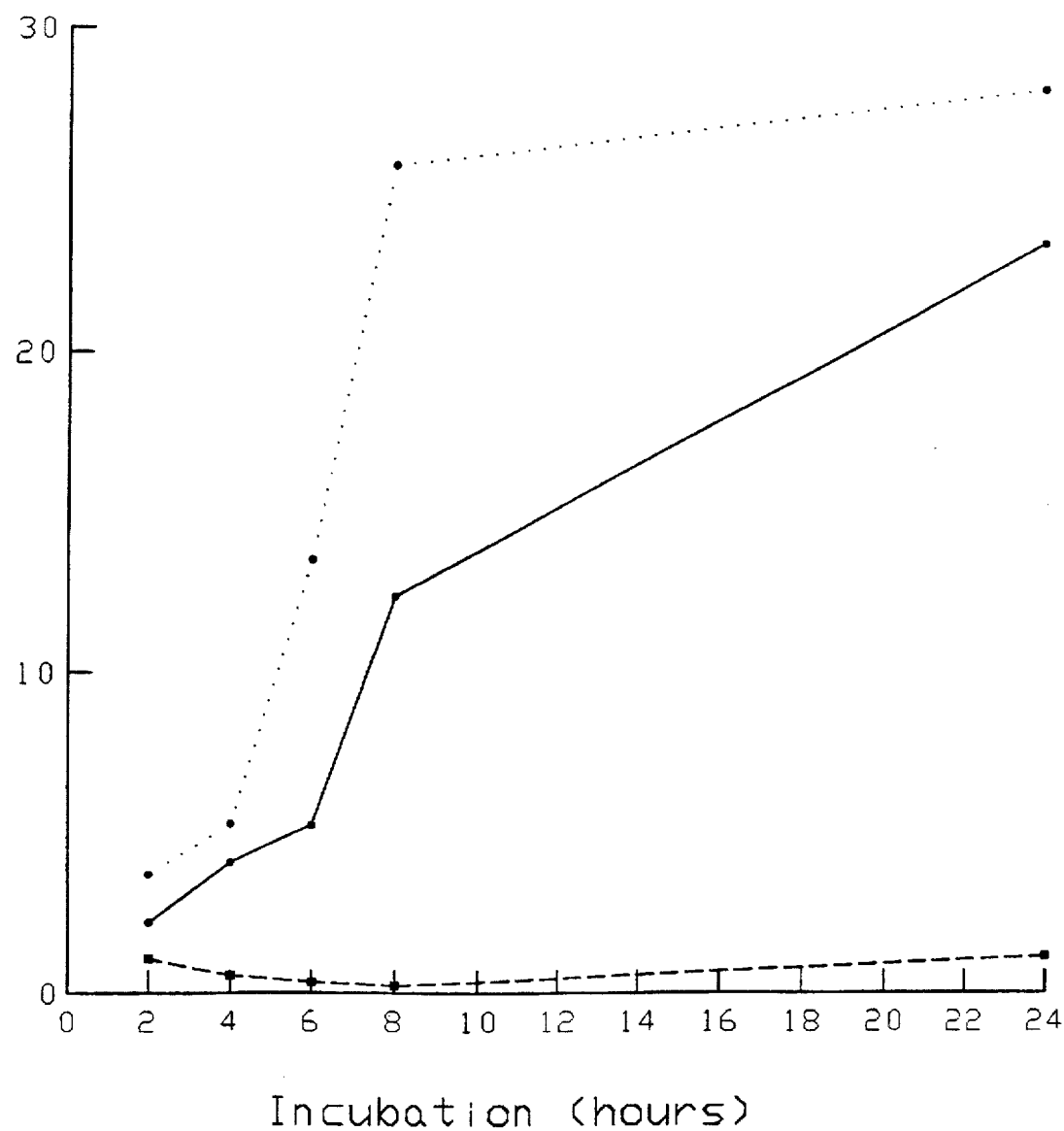
FIG. 3 shows a comparison of the effect of probucol and the compound of Example 1 when administered per os on the modification of the LDL of Watanabe Rabbits.

According to those results, which are also illustrated by FIG. 3, the peroxidation of the LDL of Watanabe rabbits treated with probucol at a dose of 250 mg/kg/day is retarded by approximately 2 hours compared with that of the control animals.

The compound of Example 1, under the same experimental conditions, completely inhibits LDL peroxidation induced by copper sulphate from a dose of 50 mg/kg/day.

3. CONCLUSION

The results reported show, on the one hand, that the compounds of the invention protect human LDL in vitro against oxidative modifications in a much more effective manner than do probucol and vitamin E, and, on the other hand, that after oral administration to the animals, the compounds bring about a protection of LDL that is very distinctly superior and of a longer duration of action compared with probucol.

We claim:

1. A substituted phenoxyisobutyric acid or ester selected from those of formula I:

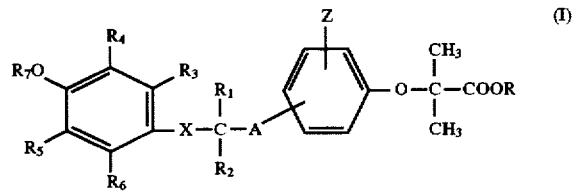

(I)

wherein:

X represents oxygen;

A represents a single bond or an alkylene radical having 1 to 9 carbon atoms inclusive in a straight or branched chain optionally including a double bond, a cyclopropyl radical, an oxygen atom or a carbonyl radical, or optionally substituted by halogen or hydroxy;

R represents hydrogen or alkyl having 1 to 6 carbon atoms inclusive in a straight or branched chain and optionally substituted by one or two hydroxy;

$R_1$ and $R_3$:
together form a $(CH_2)_n$ bridge wherein n is 1 or 2;

each of $R_2$ and $R_6$, which may be identical or different, represents hydrogen or methyl;

each of $R_4$ and $R_5$, which may be identical or different, represents alkyl having 1 to 6 carbon atoms inclusive in a straight or branched chain;

$R_7$ represents hydrogen or $CH_3CO$—, $C_2H_5O$—$CH_2$—, or benzyl; and

Z represents hydrogen, halogen, alkyl or alkoxy, each containing 1 to 5 carbon atoms inclusive in a straight branched chain;

and, when they exist, its corresponding enantiomers and diastereoisomers, and also its physiologically-tolerable salts with suitable bases.

2. A compound of claim 1 which is tert-butylamine (Z)-(R,S)-2-{4-[3-(6-hydroxy-2,5,7,8-tetramethylchroman-2-yl)prop-2-en-1-yl]phenoxy}isobutyrate.

3. A compound of claim 1 which is tert-butylamine (R,S)-2-{4-[3-(6-hydroxy-2,5,7,8-tetramethylchroman-2-yl)propyl]phenoxy}isobutyrate.

4. A pharmaceutical composition, useful for treating a pathology in which membrane lipid peroxidation plays an initiating and/or aggravating role, comprising as active ingredient an effective amount of a compound as claimed in claim 1 together with a pharmaceutically-acceptable excipient.

5. A method for treating a mammal, afflicted with a pathology in which membrane lipid peroxidation plays an initiating and/or aggravating role, comprising the step of administering to the said mammal an amount of a compound of claim 1 which is effective for alleviation of the said condition.

* * * * *

UNITED STATES PATENT AND TRADEMARK OFFICE
CERTIFICATE OF CORRECTION

PATENT NO. : 5,627,205
DATED : May 6,1997
INVENTOR(S) : Gilbert Regnier et al.

Page 1 of 2

It is certified that error appears in the above-indentified patent and that said Letters Patent is hereby corrected as shown below:

In the Title page, [56] References Cited, Publications, line 7: Change "of" to -- to -- after "Susceptibility" and change "to" to -- of -- after "Oxidation". Other Prior Art in PTO 1449 dated 8-03-95 and signed 10-9-96

Column 5, line 16: Delete "p2" before "which".

Column 5, line 27: Insert a comma -- , -- between "A"and "Z".

Column 6, line 35: Replace "$R_3$" before "and" with -- $A_3$ --.

Column 7, line 45: Insert -- $A_4$,-- before "Z".

Column 13, line 24: Delete "1," between "formyl-" and "2".

Column 14, line 46: Insert -- 5% -- after "of" at the end of the line.

UNITED STATES PATENT AND TRADEMARK OFFICE
CERTIFICATE OF CORRECTION

PATENT NO. : 5,627,205
DATED : May 22, 1997
INVENTOR(S) : Gilbert Regnier et al.

Page 2 of 2

It is certified that error appears in the above-indentified patent and that said Letters Patent is hereby corrected as shown below:

Column 16, line 6: "2-(4-[2-{4-" should read --2-{4-[2-(4-".

Column 24, line 26: Insert -- or -- between "straight" and "branched".

Signed and Sealed this

Twenty-second Day of July, 1997

Attest:

BRUCE LEHMAN

Attesting Officer

Commissioner of Patents and Trademarks